US009308226B2

(12) United States Patent
Borody (10) Patent No.: US 9,308,226 B2
(45) Date of Patent: Apr. 12, 2016

(54) COMPOSITIONS FOR FECAL FLORAL TRANSPLANTATION AND METHODS FOR MAKING AND USING THEM AND DEVICES FOR DELIVERING THEM

(76) Inventor: Thomas Julius Borody, Five Dock (AU)

( * ) Notice: Subject to any disclaimer, the term of this patent is extended or adjusted under 35 U.S.C. 154(b) by 0 days.

(21) Appl. No.: 13/813,915

(22) PCT Filed: Aug. 4, 2011

(86) PCT No.: PCT/AU2011/000987
§ 371 (c)(1),
(2), (4) Date: Apr. 8, 2013

(87) PCT Pub. No.: WO2012/016287
PCT Pub. Date: Feb. 9, 2012

(65) Prior Publication Data
US 2013/0195804 A1     Aug. 1, 2013

Related U.S. Application Data (60) Provisional application No. 61/494,363, filed on Jun. 7, 2011, provisional application No. 61/483,487, filed on May 6, 2011, provisional application No. 61/451,087, filed on Mar. 9, 2011, provisional application No. 61/450,099, filed on Mar. 7, 2011.

(30) Foreign Application Priority Data

Aug. 4, 2010   (AU) ............................... 2010903474

(51) Int. Cl.
| | |
|---|---|
| A61K 35/74 | (2015.01) |
| A61M 5/142 | (2006.01) |
| A61K 35/24 | (2015.01) |
| C12N 1/00 | (2006.01) |
| A61K 35/00 | (2006.01) |
| A61K 9/48 | (2006.01) |
| A61M 31/00 | (2006.01) |

(52) U.S. Cl.
CPC ............... *A61K 35/74* (2013.01); *A61K 35/24* (2013.01); *A61M 5/142* (2013.01); *C12N 1/00* (2013.01); *A61K 9/4875* (2013.01); *A61K 2035/115* (2013.01); *A61M 31/00* (2013.01)

(58) Field of Classification Search
None
See application file for complete search history.

(56) References Cited

U.S. PATENT DOCUMENTS

| | | | |
|---|---|---|---|
| 4,452,779 A | 6/1984 | Cockerill | |
| 4,536,409 A | 8/1985 | Farrell et al. | |
| 4,975,286 A | 12/1990 | Hechter | |
| 5,443,826 A | 8/1995 | Borody | |
| 6,162,464 A | 12/2000 | Jacob et al. | |
| 6,649,397 B1 * | 11/2003 | Nakamura | 435/243 |
| 7,541,091 B2 | 6/2009 | Sisson et al. | |
| 7,998,510 B2 | 8/2011 | Caswell | |
| 2003/0147858 A1 * | 8/2003 | Renaud et al. | 424/93.4 |
| 2004/0223956 A1 * | 11/2004 | Naidu et al. | 424/93.45 |
| 2006/0076536 A1 * | 4/2006 | Barshied | 252/188.28 |
| 2010/0255231 A1 | 10/2010 | Chau et al. | |
| 2011/0008554 A1 | 1/2011 | Chen et al. | |
| 2011/0045222 A1 | 2/2011 | Peters | |

FOREIGN PATENT DOCUMENTS

| | | |
|---|---|---|
| AU | 2001276160 B2 | 2/2002 |
| CA | 1333564 | 12/1994 |
| EP | 1514572 A2 | 3/2005 |
| JP | 5306221 | 11/1993 |
| JP | 07242539 | 9/1995 |
| WO | 9001335 | 2/1990 |
| WO | 2008077614 A2 | 7/2008 |
| WO | 2008077614 A3 | 7/2008 |
| WO | 2011033310 A1 | 3/2011 |
| WO | 2011094027 A1 | 8/2011 |

(Continued)

OTHER PUBLICATIONS

Porter, S.C. Remington: The Science and Practice of Pharmacy, Chapter 46; Hendrickson, et al., Ed.; Lippincott Williams & Wilkins: Philadelphia, PA, 2005; pp. 929-938.*
Aas et al., "Recurrent Clostridium difficile Colitis: Case Series Involving 18 Patients Treated with Donor Stool Administered via a Nasogastric Tube," Clinical Infectious Diseases, vol. 36, No. 5, Mar. 1, 2003, pp. 580-585.
Bakken, "Fecal bacteriotherapy for recurrent Clostridium difficile infection," Anaerobe, 15, 2009, pp. 285-289.
Borody et al., "Bacteriotherapy Using Fecal Flora Toying with Human Motions," J. Clin. Gastroenterol., vol. 38, No. 6, Jul. 2004, 475-483.

(Continued)

*Primary Examiner* — Renee Claytor
*Assistant Examiner* — Michelle F Paguio Frising
(74) *Attorney, Agent, or Firm* — Gregory P. Einhorn; Greer Burns & Crain Ltd.

(57) ABSTRACT

In alternative embodiments, the invention provides compositions, e.g., formulations, used for gastric, gastrointestinal and/or colonic treatments or lavage, e.g., orthostatic lavage, e.g., for inducing the purgation (e.g., cleansing) of a gastrointestinal (GI) tract, including a colon; and methods for making and using them. In alternative embodiments, compositions and methods of the invention are used for the stabilization, amelioration, treatment and/or prevention of constipation, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea, or *C. difficile* or the pseudo-membranous colitis associated with this infection. In alternative embodiments, the invention provides pharmaceuticals and products (articles) of manufacture for delivering these compositions and formulations to an individual, e.g., a human or an animal. The invention also provides devices for delivering a fecal material to a patient.

18 Claims, 2 Drawing Sheets

(56) References Cited

FOREIGN PATENT DOCUMENTS

| WO | 2011110347 A2 | 9/2011 |
| WO | 2012045150 A1 | 4/2012 |

OTHER PUBLICATIONS

Borody et al., "Treatment of Ulcerative Colitis Using Fecal Bacteriotherapy," J. Clin. Gastroenterol., 2003; 37(1):42-47.

Floch, "Fecal Bacteriotherapy, Fecal Transplant, and the Microbiome," J. Clin. Gastroenterol., vol. 44, No. 8, Sep. 2010, 529-530.

Gustafsson et al., "Faecal Short-Chain Fatty Acids in Patients with Antibiotic-Associated Diarrhoea, before and after Faecal Enema Treatment," Scand J Gastroenterol, 1998; 33:721-727.

Lever, K., International Preliminary Report on Patentability, PCT/AU2011/000987, Australian Patent Office, Dec. 12, 2012.

Lever, K., International Search Report, PCT/AU2011/000987, Australian Patent Office, Oct. 28, 2011.

Lever, K., Written Opinion of the International Searching Authority, PCT/AU2011/000987, Australian Patent Office, Oct. 28, 2011.

Lund-Tonnesen et al., "Clostridium difficile-assosiert diare behandlet med homolog feces," Tidsskr Nor Laegeforen nr. 7, 1998; 118:1027-30.

van Nood et al., "Struggling with Recurrent Clostridium Difficile Infections: Is Donor Faeces the Solution?", Euro Surveill., 2009, 14(3), pp. 1-6.

Schiller, "Review article" the therapy of constipation, Ailment Pharmacol. Ther., 2001, 15:749-763.

Schwan et al., "Relapsing Clostridium difficile Enterocolitis Cured by Rectal Infusion of Normal Faeces," Scand J Infect Dis, 16: 211-215, 1984.

Tvede et al., "Bacteriotherapy for Chronic Relapsing Clostridium Difficile Diarrhoea in Six Patients," The Lancet, May 27, 1989, pp. 1156-1160.

Lever, Kerry, International Preliminary Report on Patentability, PCT/AU2011/000987, Australian Patent Office, Date of Completion of Report: Dec. 12, 2012.

Zulhendri, Felix, First Office Action, New Zealand Patent Office, IP No. 607043, Oct. 15, 2013.

Dan, M. et al "Comparison of preservation media and freezing conditions for storage of specimens of faeces", J. Med Microbiology, vol. 28 (Feb. 1989), 151-154.

Frantzen M.A.J. et al, "Empirical evaluation of preservation methods for faecal DNA", Molecular Ecology (Oct. 1998) 7(10), 1423-1428.

Grehan, Martin J et al, "Durable alteration of the colonic microbiota by the administration of donor fecal flora", Journal of Clinical Gastroenterology, Sep. 2010—vol. 44, Issue 8, pp. 551-561.

Sonia Yoon and Lawrence Brandt, "Treatment of refractory/recurrent C. difficile-associated disease by donated stool transplanted via colonoscopy: A case series of 12 patents", Journal of Clinical Gastroenterology, Sep. 2010—vol. 44, issue 8, pp. 562-566.

Chinese Office Action No. 2011800463050, Aug. 4, 2011.

Crowther, J.S. "Transport and storage of faeces for bacteriological examination", Journal of Applied Bacteriology Jun. 1971, 34 (2), 477-483.

Merckling-Ruiz, V., Extended European Search Report, European Patent Application No. 11813951.8, Apr. 3, 2014.

* cited by examiner

COMPOSITIONS FOR FECAL FLORAL TRANSPLANTATION AND METHODS FOR MAKING AND USING THEM AND DEVICES FOR DELIVERING THEM

This application is a national phase application claiming benefit of priority under 35 U.S.C. §371 to International (PCT) Patent Application serial number PCT/AU2011/000987, filed Aug. 4, 2011, which claims benefit of priority to AU2010903474, filed Aug. 4, 2010. The aforementioned applications are expressly incorporated herein by reference in their entirety and for all purposes.

TECHNICAL FIELD

This invention generally relates to medicine and gastroenterology, pharmacology and microbiology. In alternative embodiments, the invention provides compositions, e.g., formulations or preparations, and devices, used for the transplantation of a treated or isolated fecal flora, and methods for making and using them. In alternative embodiments, compositions, devices and methods of the invention can be used for any gastric, gastrointestinal and or colonic treatment or lavage. In alternative embodiments, compositions, devices and methods of the invention are used for the amelioration, stabilization, treatment and/or prevention of a disease or a condition such as constipation, Crohn's Disease, exposure to a poison or a toxin or for an infection, e.g., a toxin-mediated travellers diarrhea; or any bowel disease or condition having a bowel dysfunction component, for example, an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, or a pancreatic insufficiency. In alternative embodiments, the invention provides pharmaceuticals and products (articles) of manufacture for delivering these compositions and formulations to an individual, e.g., a human or an animal. The invention also provides devices for delivering a fecal material to an individual, e.g., a patient.

BACKGROUND

Bacterial flora of the bowel has recently gained importance from a therapeutic point of view. It is now realized that the human flora, rather than just being waste material resulting from digestion of food, is an important virtual organ containing large numbers of living microorganisms. There are in excess of one hundred thousand different subspecies—or more—arranged in families and subgroups of genetically different but often linearly related organisms. The waste "material" makes up a proportion of the flora. The bacterial content of the flora is actively breaking down or metabolizing the non-absorbed matter, largely fiber, on which the bacterial cells grow. Because the bacterial flora is contained within the human body and is made up of living components it constitutes in fact as a living organ or a virtual organ.

This virtual organ can be healthy in that it doesn't contain any pathogenic organisms, or it can become infected or infested with parasite, bacteria or viruses. When infected with some pathogenic species, such infecting species can manufacture molecules that affect secretion, which can cause pain, or can paralyze the bowel causing constipation. Infection of the bowel flora or bowel flora organ can impact the health of the individual.

Many of these infections can be acute, such as cholera, but some can be chronic and can really impact on the life of the individual carrying the infected flora. For example, after antibiotic therapy some of the families of the bacteria can be suppressed or eradicated and infectious agents such as *Clostridium difficile* and other pathogens can lodge and become passengers within the human flora. These 'passengers' are also pathogenic because they can produce toxins e.g. toxins A and B for *C. difficile*.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

SUMMARY

According to a first aspect of the present invention, there is provided a delivery vehicle, formulation, composition, pharmaceutical preparation, product of manufacture, container or device, comprising: an entire (or substantially entire) microbiota; a treated or untreated fecal flora; a complete or partial fecal flora, a fecal flora substantially or completely purified of non-fecal floral fecal material, or a partially, substantially or completely isolated or purified fecal flora, made by a process comprising:

(i) providing an entire (or substantially entire) microbiota, a treated or untreated fecal flora sample, a complete or partial fecal flora sample, a fecal flora substantially or completely purified of non-fecal floral fecal material or a partially, substantially or completely isolated or purified fecal flora; and, a delivery vehicle, formulation, pharmaceutical preparation, composition, product of manufacture, container or device, and (ii) placing the entire (or substantially entire) microbiota, the treated or untreated fecal flora sample, the complete or partial fecal flora sample, the fecal flora substantially or completely purified of non-fecal floral fecal material, or the partially, substantially or completely isolated or purified fecal flora in the delivery vehicle, formulation, composition, pharmaceutical preparation, product of manufacture, container or device.

According to a second aspect of the present invention, there is provided a product (article) of manufacture comprising a delivery vehicle, formulation, composition pharmaceutical preparation, container or device of the first aspect.

According to a third aspect of the present invention, there is provided a method for making a delivery vehicle, formulation, composition pharmaceutical preparation, product of manufacture, container or device according to the first or second aspect comprising (i) providing: an entire (or substantially entire) microbiota; a treated or untreated fecal sample; a complete or partial fecal flora sample, a fecal flora substantially or completely purified of non-fecal floral fecal material or a partially, substantially or completely isolated or purified fecal flora; and, a delivery vehicle, formulation, pharmaceutical preparation, composition product of manufacture, container or device, and (ii) placing the entire (or substantially entire) microbiota, treated or untreated fecal sample, the complete or partial fecal flora, the fecal flora substantially or completely purified of non-fecal floral fecal material or the partially, substantially or completely isolated or purified fecal flora in the delivery vehicle, formulation, pharmaceutical preparation, composition, product of manufacture, container or device, and creating a substantially or completely oxygen-free environment in the container or device.

According to a fourth aspect of the present invention there is provided a method for the amelioration, stabilization, treatment and/or prevention of an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated traveler's diarrhea, or a *Clostridium* or a *C. perfringens* welchii or a *C. difficile* infection or a pseudo-membranous colitis associated with a *Clostridium* infection, comprising:

administering to an individual in need thereof via a delivery vehicle, formulation, composition, pharmaceutical preparation, product of manufacture, container or device of the first aspect, or a product (article) of manufacture of the second aspect the entire (or substantially entire) microbiota, the treated or untreated fecal flora sample, the complete or partial fecal flora sample, the fecal flora substantially or completely purified of non-fecal floral fecal material, or the partially, substantially or completely isolated or purified fecal flora.

According to a fifth aspect of the present invention, there is provided a delivery vehicle, formulation, composition, pharmaceutical preparation, product of manufacture, container or device comprising:

an entire (or substantially entire) microbiota; a partially, substantially or completely isolated or purified fecal flora; or, a composition comprising a fecal flora substantially or a completely purified of non-fecal floral fecal material.

According to a sixth aspect of the present invention, there is provided a method for the amelioration, stabilization, treatment and/or prevention of an infection, disease, treatment, poisoning or a condition having a bowel dysfunction component or side-effect comprising administering to an individual in need thereof via a delivery vehicle, formulation, composition, pharmaceutical preparation, product of manufacture, container or device according to the fifth aspect the entire (or substantially entire) microbiota, the partially, substantially or completely isolated or purified fecal flora, or the composition comprising a fecal flora substantially or a completely purified of non-fecal floral fecal material.

Figure 1A:
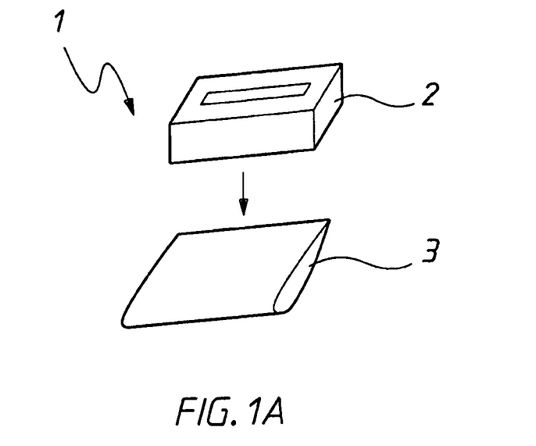
FIG. 1A illustrates an exemplary storage device of the invention; and, FIG. 1B illustrates an exemplary delivery device of the invention, as described below.
Figure 1B:
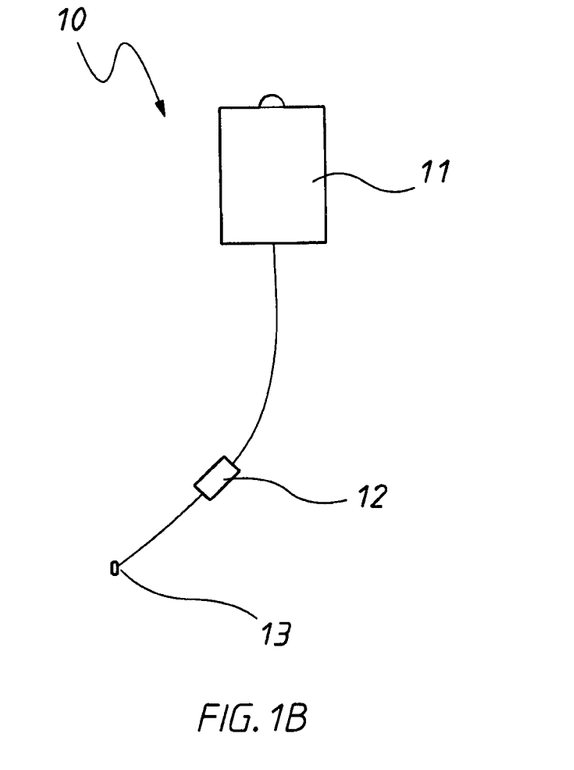
Figure 2:
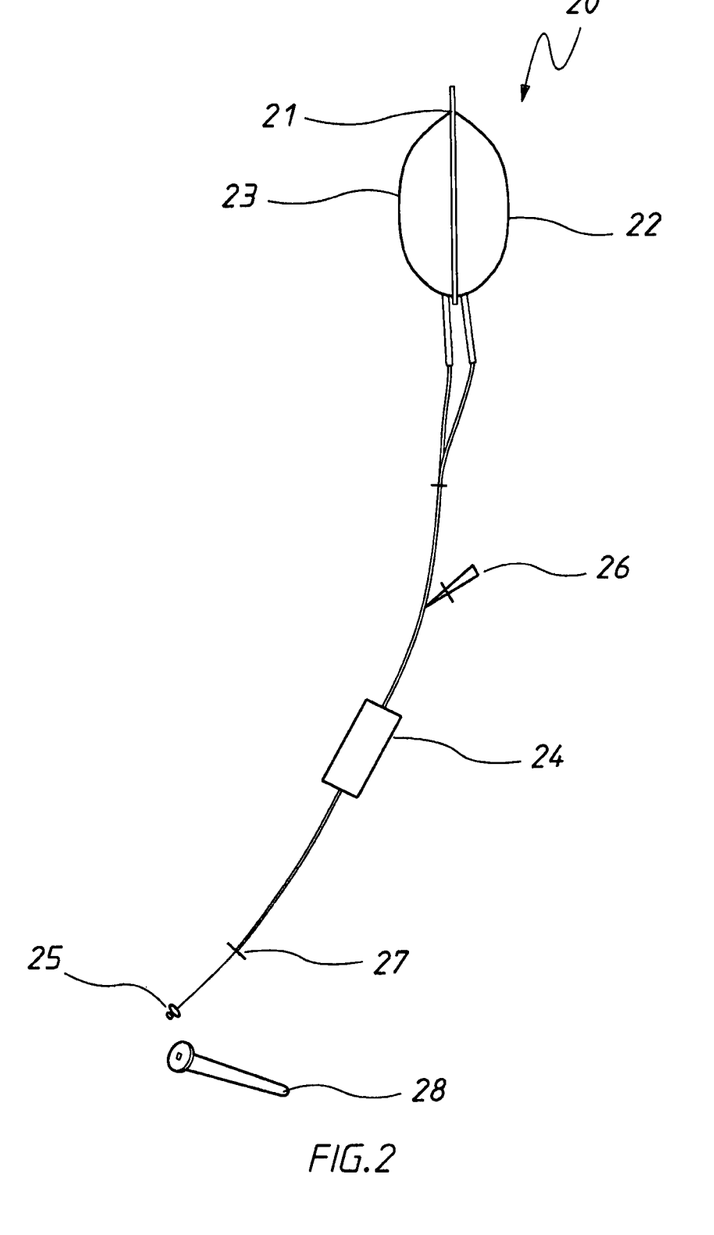
FIG. 2 illustrates an exemplary delivery device of the invention.

According to a seventh aspect of the present invention, there is provided a device for delivering a fecal material or a composition of the first aspect, comprising:

(a) a device as illustrated in FIG. 1B or FIG. 2; or
(b) a device comprising
   (i) a bag or container comprising an exit aperture operably connected to the proximal end of a flexible tube or equivalent,
   (ii) an open or close valve or equivalent or an obdurator screwtop at the distal end of the flexible tube or equivalent, and
   (iii) a pump, or a hand pump, for moving material in the bag or container through the flexible tube or equivalent and out the distal end or out the open or close valve or equivalent; or
(c) the device of (a) or (b), further comprising a fecal material or a composition of the first aspect.

According to an eighth aspect of the present invention, there is provided a bag or container comprising: an entire (or substantially entire) microbiota; a treated or untreated fecal flora; a complete or partial fecal flora, a fecal flora substantially or completely purified of non-fecal floral material or, a partially, substantially or completely isolated or purified fecal flora, or a composition thereof wherein the bag or container is structurally the same as or similar to a bag or container of a device of the seventh aspect.

According to a ninth aspect of the present invention, there is provided a method for the amelioration, stabilization, treatment and/or prevention of, or decreasing or delaying the symptoms of, an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated travellers diarrhea, or a *Clostridium* or a *C. perfringens* welchii or a *C. difficile* infection or a pseudo-membranous colitis associated with a *Clostridium* infection, or for preventing, or decreasing or delaying the symptoms of, or ameliorating or treating individuals with spondyloarthropatliy, spondylarthritis or sacrolileitis (an inflammation of one or both sacroiliac joints); a nephritis syndrome; an inflammatory or an autoimmune condition having a gut or an intestinal component; lupus; irritable bowel syndrome (IBS or spastic colon); or a colitis; Ulcerative Colitis or Crohn's Colitis; constipation; autism; a degenerative neurological diseases; amyotrophic lateral sclerosis (ALS), Multiple Sclerosis (MS) or Parkinson's Disease (PD); a Myoclonus Dystonia;, Steinert's disease; proximal myotonic myopathy; an autoimmune disease; Rheumatoid Arthritis (RA) or juvenile idiopathic arthritis (JIA); Chronic Fatigue Syndrome; benign myalgic encephalomyelitis; chronic fatigue immune dysfunction syndrome; chronic infectious mononucleosis; epidemic myalgic encephalomyelitis; obesity; hypoglycemia, pre-diabetic syndrome, type I diabetes or type II diabetes; Idiopathic thrombocytopenic purpura (ITP); an acute or chronic allergic reaction; hives, a rash, a urticaria or a chronic urticaria; and/or insomnia or chronic insomnia, Grand mal seizures or petit mal seizures, comprising:

administering to an individual in need thereof via a delivery vehicle, formulation, pharmaceutical preparation, product of manufacture, container or device of the first aspect or a product (article) of manufacture of the second aspect of the entire (or substantially entire) microbiota, the treated or untreated fecal flora sample, the complete or partial fecal flora sample, the fecal flora substantially or completely purified of non-fecal floral fecal material, or the partially, substantially or completely isolated or purified fecal flora, in single, repeat or multiple administrations, deliveries or infusions.

According to a tenth aspect of the present invention, there is provided an entire (or substantially entire) microbiota, a treated or untreated fecal flora sample, a complete or partial fecal flora sample, a fecal flora substantially or completely purified of non-fecal floral fecal material, or a partially, substantially or completely isolated or purified fecal flora for use in the amelioration, stabilization, treatment and/or prevention of an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated travelers diarrhea, or a *Clostridium* or a *C. perfringens* welchii or a *C. difficile* infection or a pseudo-membranous colitis associated with a *Clostridium* infection.

According to an eleventh aspect of the present invention, there is provided use of an entire (or substantially entire) microbiota, a treated or untreated fecal flora sample, a complete or partial fecal flora sample, a fecal flora substantially or completely purified of non-fecal floral fecal material, or a partially, substantially or completely isolated or purified fecal flora in the preparation of a medicament for the amelioration, stabilization, treatment and/or prevention of an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated travelers diarrhea, or a *Clostridium* or a *C. perfringens* welchii or a *C. difficile* infection or a pseudo-membranous colitis associated with a *Clostridium* infection.

According to a twelfth aspect of the present invention, there is provided use of a device of the seventh aspect for delivering a fecal material or an entire (or substantially entire) microbiota, a treated or untreated fecal flora sample, a complete or partial fecal flora sample, a fecal flora substantially or completely purified of non-fecal floral fecal material, or a partially, substantially or completely isolated or purified fecal flora in the amelioration, stabilization, treatment and/or prevention of an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated travelers diarrhea, or a *Clostridium* or a *C. perfringens* welchii or a *C. difficile* infection or a pseudo-membranous colitis associated with a *Clostridium* infection.

In alternative embodiments, the invention provides compositions (including formulations, pharmaceutical compositions, foods, feeds, supplements, products of manufacture, and the like) comprising: delivery vehicle, formulation, container or device, comprising a treated or untreated fecal flora, or a partially, substantially or completely isolated fecal flora; and methods of making and using them.

In alternative embodiments, the invention provides delivery vehicles, formulations, pharmaceutical preparations, products of manufacture, containers or devices, comprising: a treated or untreated fecal flora, an entire (or substantially entire) microbiota, and/or a partially, substantially or completely isolated fecal flora, made by a process comprising:

(a) (i) providing a treated or untreated fecal sample, or a sample comprising an entire (or substantially entire) microbiota, or a composition comprising a complete or partial fecal flora, or a partially, substantially or completely isolated or purified fecal flora; and, a delivery vehicle, formulation, pharmaceutical preparation, product of manufacture, container or device, and (ii) placing the treated or untreated fecal sample, the partially, substantially or completely isolated or purified fecal flora, the entire (or substantially entire) microbiota, or a composition comprising a complete or partial fecal flora or partially, substantially or completely isolated or purified fecal flora, in the delivery vehicle, formulation, pharmaceutical preparation, product of manufacture, container or device, and optionally creating a substantially or completely oxygen-free environment in the delivery vehicle, formulation, pharmaceutical preparation, product of manufacture, container or device, and optionally the delivery vehicle, formulation, pharmaceutical preparation, product of manufacture, container or device is sterile or bacteria-free before the placing of the treated or untreated fecal sample, or the partially, substantially or completely isolated or purified fecal flora;

(b) the delivery vehicle, formulation, pharmaceutical preparation, product of manufacture, container or device of (a), wherein the delivery vehicle, formulation, pharmaceutical preparation, product of manufacture, container or device is made substantially or completely oxygen free (e.g., at least about 90%, 91%, 92%, 93%, 94%, 95%, 96%, 97%, 98%, 99%, 99.5%, 99.6%, 99.7%, 99.8% or 99.9% oxygen free) by: incorporating into the delivery vehicle, formulation, pharmaceutical preparation, product of manufacture, container or device a built in or clipped-on oxygen-scavenging mechanism; and/or, the delivery vehicle, formulation, pharmaceutical preparation, product of manufacture, container or device comprises or is coated with an oxygen scavenging material; and/or completely or substantially replacing the air in the delivery vehicle, formulation, pharmaceutical preparation, product of manufacture, container or device with nitrogen and/or other inert non-reactive gas or gases;

(c) the delivery vehicle, formulation, pharmaceutical preparation, product of manufacture, container or device of (a) or (b), wherein the delivery vehicle, formulation, pharmaceutical preparation, product of manufacture, container or device simulates (creates) partially, substantially or completely an anaerobic environment;

(d) the delivery vehicle, formulation, pharmaceutical preparation, product of manufacture, container or device of any, of (a) to (c), wherein the delivery vehicle, formulation, pharmaceutical preparation, product of manufacture, container or device is manufactured, labelled or formulated for human or animal use;

(e) the delivery vehicle, formulation, pharmaceutical preparation, product of manufacture, container or device of (d), wherein the animal use is for a veterinary use;

(f) the delivery vehicle, formulation, pharmaceutical preparation, product of manufacture, container or device of any of (a) to (e), wherein a stabilizing agent or a glycerol is added to, or mixed into, the treated or untreated fecal sample, entire (or substantially entire) microbiota, or partially, substantially or completely isolated fecal flora, before storage or freezing, spray-drying, freeze-drying or lyophilizing;

(g) the delivery vehicle, formulation, pharmaceutical preparation, product of manufacture, container or device of any of (a) to (f), wherein the delivery vehicle, formulation, pharmaceutical preparation, product of manufacture, container or device is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation;

(h) the delivery vehicle, formulation, pharmaceutical preparation, product of manufacture, container or device of any of (a) to (g), wherein the fecal sample is treated such that the fecal flora is separated from rough particulate matter in the fecal sample by: homogenizing, centrifuging and/or filtering a rough particulate matter or a non-floral matter of the fecal material, or by plasmapheresis, centrifugation, centrifuge, column chromatography (e.g., affinity chromatography), immunoprecipitation (e.g., antibodies fixed to a solid surface, such as beads or a plate);

(i) the delivery vehicle, formulation, pharmaceutical preparation, product of manufacture, container or device of any of (a) to (h), wherein the treated or untreated fecal flora, entire (or substantially entire) microbiota, or partially, substantially or completely isolated or purified fecal flora, is lyophilized, freeze-dried or frozen, or processed into a powder;

(j) the delivery vehicle, formulation, pharmaceutical preparation, product of manufacture, container or device of any of (a) to (i), wherein the fecal flora (including e.g., the entire (or substantially entire) microbiota) is initially derived from an individual screened or tested for a disease or infection, and/or the fecal flora is initially derived from an individual screened to have a normal, healthy or wild type population of fecal flora;

(k) the delivery vehicle, formulation, pharmaceutical preparation, product of manufacture, container or device of any of (a) to (j), wherein a substantially isolated or a purified fecal flora or entire (or substantially entire) microbiota is (comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or (l) the delivery vehicle, formulation, pharmaceutical preparation, product of manufacture, container or device of any of (a) to (j), wherein the amount of the treated or untreated fecal sample, entire (or substantially entire) microbiota, or the partially, substantially or completely isolated or purified fecal flora is formulated for or calibrated for repeat or multiple delivery or infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the delivery vehicle, formulation, pharmaceutical preparation, product of manufacture, container or device of the invention further comprises:

a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavouring agent, a pH stabilizer, an acidifying agent, a preservative, a desweetening agent and/or colouring agent;

at least one vitamin, mineral and/or dietary supplement, wherein optionally the vitamin comprises a thiamine, riboflavin, nicotinic acid, pantothenic acid, pyridoxine, biotin, folic acid, vitamin B12, lipoic acid, ascorbic acid, vitamin A, vitamin D, vitamin E, vitamin K, a choline, a carnitine, and/or an alpha, beta and/or gamma carotene; or a prebiotic nutrient, wherein optionally the prebiotic comprises any ingredient that stimulates the stability, growth and/or activity of the fecal flora or fecal bacteria, or optionally comprises polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides.

In alternative embodiments, the invention provides products (articles) of manufacture comprising a delivery vehicle, formulation, pharmaceutical preparation, container or device of the invention.

In alternative embodiments, the invention provides methods for making a delivery vehicle, formulation, pharmaceutical preparation, product of manufacture, container or device, comprising a treated or untreated fecal flora, entire (or substantially entire) microbiota, or a partially, substantially or completely isolated or purified fecal flora, comprising:

(a) (i) providing a treated or untreated fecal sample, or a composition comprising a complete or partial fecal flora, an entire (or substantially entire) microbiota, or a partially, substantially or completely isolated or purified fecal flora; and, a delivery vehicle, formulation, pharmaceutical preparation, product of manufacture, container or device, and (ii) placing the treated or untreated fecal sample, the partially, substantially or completely isolated or purified fecal flora, the entire (or substantially entire) microbiota, or a composition comprising a complete or partial fecal flora or partially, substantially or completely isolated or purified fecal flora, in the delivery vehicle, formulation, pharmaceutical preparation, product of manufacture, container or device, and creating a substantially or completely oxygen-free environment in the container or device;

(b) the method of (a), wherein the delivery vehicle, formulation, pharmaceutical preparation, product of manufacture, container or device is made substantially or completely oxygen free by: incorporating into the delivery vehicle, formulation, container or device a built in or clipped-on oxygen-scavenging mechanism; and/or, the delivery vehicle, formulation, pharmaceutical preparation, product of manufacture, container or device comprises or is coated with an oxygen scavenging material; and/or completely or substantially replacing the air in the delivery vehicle, formulation, pharmaceutical preparation, product of manufacture, container or device with nitrogen and/or other inert non-reactive gas or gases;

(c) the method of (a) or (b), wherein the delivery vehicle, formulation, pharmaceutical preparation, product of manufacture, container or device simulates (creates) partially, substantially or completely an anaerobic environment;

(d) the method of any of (a) to (c), wherein the delivery vehicle, formulation, pharmaceutical preparation, product of manufacture, container or device is manufactured, labelled or formulated for human or animal use;

(e) the method of (d), wherein the animal use is for a veterinary use;

(f) the method of any of (a) to (e), wherein a prebiotic, a stabilizing agent or a glycerol is added to, or mixed into, the treated or untreated fecal sample, or partially, substantially or completely isolated or purified fecal flora, before storage or freeze-drying, spray-drying, freezing or lyophilizing;

(g) the method of any of (a) to (f), wherein the delivery vehicle, formulation, pharmaceutical preparation, product of manufacture, container or device is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation;

(h) the method of any of (a) to (g), wherein the fecal sample is treated such that the fecal flora is separated from rough particulate matter in the fecal sample by: homogenizing, centrifuging and/or filtering a rough particulate matter or a non-floral matter of the fecal material, or by plasmapheresis, centrifugation, celltrifuge, column chromatography (e.g., affinity chromatography), immunoprecipitation (e.g., antibodies fixed to a solid surface, such as beads or a plate);

(i) the method of any of (a) to (h), wherein the treated or untreated fecal flora, or partially, substantially or completely isolated or purified fecal flora, is lyophilized, freeze-dried or frozen, or processed into a powder;

(j) the method of any of (a) to (i), wherein the fecal flora is initially derived from an individual screened or tested for a disease or infection, and/or the fecal flora is initially derived from an individual screened to have a normal, healthy or wild type population of fecal flora; or (k) the method of any of (a) to (j), further comprising adding to the treated or untreated fecal flora, or adding to a liquid or solution used to isolate or purify, store, freeze, freeze-dry, spray-dry, lyophilize, transport, reconstitute and/or deliver a treated or untreated fecal flora (optionally an entire (or substantially entire) microbiota, a partially, substantially or completely isolated or purified fecal flora, or a composition comprising a fecal flora substantially or completely purified of non-fecal floral fecal material of the invention):

a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavouring agent, a pH stabilizer, an acidifying agent, a preservative, a desweetening agent and/or colouring agent, and/or at least one vitamin, mineral and/or dietary supplement, wherein optionally the vitamin comprises a thiamine, riboflavin, nicotinic acid, pantothenic acid, pyridoxine, biotin, folic acid, vitamin $B_{12}$, lipoic acid, ascorbic acid, vitamin A, vitamin D, vitamin E, vitamin K, a choline, a carnitine, and/or an alpha, beta and/or gamma carotene, and/or a prebiotic nutrient, wherein optionally the prebiotic comprises any ingredient that stimulates the stability, growth and/or activity of the fecal flora or fecal bacteria, or optionally comprises polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides;

(l) the method of any of (a) to (k), wherein an entire (or substantially entire) microbiota, a substantially isolated or a purified fecal flora is (comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or (m) the method of any of (a) to (l), wherein the amount of the entire (or substantially entire) microbiota, the treated or untreated fecal sample, or the partially, substantially or completely isolated or purified fecal flora is formulated for or calibrated for repeat or multiple delivery or infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides methods for the amelioration, stabilization, treatment and/or prevention of an infection, disease, treatment, poisoning or a condition having a bowel dysfunction component or side-effect, or for the amelioration, stabilization, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated travellers diarrhea, or a *Clostridium* or a *C. difficile* or a pseudo-membranous colitis associated with a *Clostridium* infection, comprising administering to an individual in need thereof a delivery vehicle, formulation, pharmaceutical preparation, product of manufacture, container or device of the invention, or a product (article) of manufacture of the invention.

In alternative embodiments, the invention provides methods for the amelioration, stabilization, treatment and/or prevention of an infection, disease, treatment, poisoning or a condition having a bowel dysfunction component or side-effect comprising administering to an individual in need thereof a delivery vehicle, formulation, pharmaceutical preparation, product of manufacture, container or device of the invention, or a product (article) of manufacture of the invention, or their contents (e.g., the bacterial flora contained therein).

In alternative embodiments, the amount of the treated or untreated fecal sample, or the partially, substantially or completely isolated or purified fecal flora is formulated for or calibrated for repeat or multiple delivery or infusions; or the partially, substantially or completely isolated or purified fecal flora is delivered in repeated or multiple infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, of the methods the infection, disease, treatment, poisoning or condition having a bowel dysfunction component or side-effect comprises an inflammatory bowel disease (IBD), Crohn's disease, hepatic encephalopathy, enteritis, colitis, Irritable Bowel Syndrome (IBS), fibromyalgia (FM), chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, a pancreatic insufficiency, exposure to a poison or a toxin or for an infection, a toxin-mediated traveller's diarrhea, a poisoning, a pseudomembranous colitis, a *Clostridium* infection, a *C. perfringens* welchii or a *Clostridium difficile* infection, a neurological condition, Parkinson's disease, myoclonus dystonia, autism, amyotrophic lateral sclerosis, multiple sclerosis, Grand mal seizures or petit mal seizures. In alternative embodiments, the amount of the treated or untreated fecal sample, or the partially, substantially or completely isolated or purified fecal flora, is formulated for or calibrated for repeat or multiple delivery or infusions; or the treated or untreated fecal sample or the partially, substantially or completely isolated or purified fecal flora is delivered in repeated or multiple infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides delivery vehicles, formulations, pharmaceutical preparations, products of manufacture, containers or devices comprising:

(a) an entire (or substantially entire) microbiota, a partially, substantially or completely isolated or purified fecal flora, or a composition comprising a fecal flora substantially or completely purified of non-fecal floral fecal material, and optionally further comprising an excipient, or a fluid, a saline, a buffer, a buffering agent or a media, or a fluid-glucose-cellobiose agar (RGCA) media;

(b) the composition, container or device, formulation, or product of manufacture of (a), wherein the entire (or substantially entire) microbiota or the fecal flora is isolated or purified from a human or an animal fecal material;

(c) the composition, container or device, formulation, or product of manufacture of (a) or (b), wherein the entire (or substantially entire) microbiota or the fecal flora is isolated or purified using a method or protocol comprising use of a centrifuge, a centrifuge, a column or an immuno-affinity column, or wherein the entire (or substantially entire) microbiota or the fecal flora is isolated or purified by a method comprising homogenizing, centrifuging and/or filtering a rough particulate matter or a non-floral matter of the fecal material, or by plasmapheresis, centrifugation, centrifuge, column chromatography (e.g., affinity chromatography), immunoprecipitation (e.g., antibodies fixed to a solid surface, such as beads or a plate);

(d) the composition, container or device, formulation, or product of manufacture of any of (a) to (c), wherein the entire (or substantially entire) microbiota or the substantially or completely isolated or purified fecal flora, or the fecal flora substantially or completely purified of non-fecal floral fecal material, is in a substantially or completely oxygen-free environment in the composition, container or device, formulation, or product of manufacture;

(e) the delivery vehicle, formulation, container or device of (d), wherein the composition, container or device, formulation, or product of manufacture is made substantially or completely oxygen free by: incorporating into the delivery vehicle, formulation, container or device a built in or clipped-on oxygen-scavenging mechanism; and/or, the delivery vehicle, formulation, container or device comprises or is coated with an oxygen scavenging material; and/or completely or substantially replacing the air in the delivery vehicle, formulation, container or device with nitrogen and/or other inert non-reactive gas or gases;

(f) the composition, container or device, formulation, or product of manufacture of any of (a) to (c), wherein the entire (or substantially entire) microbiota, the substantially or completely isolated or purified fecal flora, or the fecal flora substantially or completely purified of non-fecal floral fecal material, is in a substantially or completely anaerobic environment;

(g) the composition, container or device, formulation, or product of manufacture of any of (a) to (f), wherein the delivery vehicle, formulation, container or device is manufactured, labelled or formulated for human or animal use;

(h) the composition, container or device, formulation, or product of manufacture of (g), wherein the animal use is for a veterinary use;

(i) the composition, container or device, formulation, or product of manufacture of any of (a) to (h), wherein a stabilizing agent or a glycerol is added to, or mixed into, the entire (or substantially entire) microbiota, or the partially, substantially or completely isolated or purified fecal flora, or the composition comprising a fecal flora substantially or completely purified of non-fecal floral fecal material, before storage or freezing, freeze-drying, spray-drying or lyophilizing;

(j) the composition, container or device, formulation, or product of manufacture of any of (a) to (f), wherein the composition, container or device, formulation, or product of manufacture is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation;

(k) the composition, container or device, formulation, or product of manufacture of any of (a) to (j), wherein the entire (or substantially entire) microbiota, or the partially, substantially or completely isolated or purified fecal flora, or the composition comprising a fecal flora substantially or completely purified of non-fecal floral fecal material, is lyophilized, freeze-dried, in powder form, or frozen;

(l) the composition, container or device, formulation, or product of manufacture of any of (a) to (k), wherein the entire (or substantially entire) microbiota or the fecal flora is initially derived from an individual screened or tested for a disease or infection, and/or the entire (or substantially entire) microbiota or the fecal flora is initially derived from an individual screened to have a normal, healthy or wild type population of fecal flora; or (m) the composition, container or device, formulation, or product of manufacture of any of (a) to (l), further comprising adding to the entire (or substantially entire) microbiota, the partially, substantially or completely isolated or purified fecal flora, or a composition comprising a fecal flora substantially or completely purified of non-fecal floral fecal material, or adding to a liquid or solution used to isolate or purify, store, freeze, freeze-dry, spray-dry, lyophilize, transport, reconstitute and/or deliver a treated or untreated fecal flora:

a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavouring agent, a pH stabilizer, an acidifying agent, a preservative, a desweetening agent and/or colouring agent, and/or at least one vitamin, mineral and/or dietary supplement, wherein optionally the vitamin comprises a thiamine, riboflavin, nicotinic acid, pantothenic acid, pyridoxine, biotin, folic acid, vitamin $B_{12}$, lipoic acid, ascorbic acid, vitamin A, vitamin D, vitamin E, vitamin K, a choline, a camitine, and/or an alpha, beta and/or gamma carotene, and/or a prebiotic nutrient, wherein optionally the prebiotic comprises any ingredient that stimulates the stability, growth and/or activity of the entire (or substantially entire) microbiota or the fecal flora or fecal bacteria, or optionally comprises polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides;

(n) the composition, container or device, formulation, or product of manufacture of any of (a) to (m), wherein a substantially isolated or a purified fecal flora is (comprises) an isolate of the entire (or substantially entire) microbiota or fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or (m) the composition, container or device, formulation, or product of manufacture of any of (a) to (l), wherein the amount of the entire (or substantially entire) microbiota or the treated or untreated fecal sample, or the partially, substantially or completely isolated or purified fecal flora is formulated for or calibrated for repeat or multiple delivery or infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides methods for the amelioration, stabilization, treatment and/or prevention of an infection, disease, treatment, poisoning or a condition having a bowel dysfunction component or side-effect comprising administering to an individual in need thereof a composition, container or device, formulation, or product of manufacture of the invention.

In alternative embodiments, of the methods the infection, disease, treatment, poisoning or condition having a bowel dysfunction component or side-effect comprises an inflammatory bowel disease (IED), Crohn's disease, hepatic encephalopathy, enteritis, colitis, irritable bowel syndrome (IES), fibromyalgia (FM), chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, a pancreatic insufficiency, exposure to a poison or a toxin or for an infection, a toxin-mediated travellers diarrhea, a poisoning, a pseudomembranous colitis, a *Clostridium* infection, a *C. perfringens* welchii or a *Clostridium difficile* infection, a neurological condition, Parkinson's disease, myoclonus dystonia, autism, amyotrophic lateral sclerosis, multiple sclerosis, Grand mal seizures or petit mal seizures.

In alternative embodiments, the invention provides methods for the amelioration, stabilization, treatment and/or prevention of, or decreasing or delaying the symptoms of, an infection, disease, treatment, poisoning or a condition having a bowel dysfunction component or side-effect, or for the amelioration, treatment and/or prevention of a constipation, for the treatment of an abdominal pain, a non-specific abdominal pain or a diarrhea, a diarrhea caused by: a drug side effect or a psychological condition or Crohn's Disease, a poison, a toxin or an infection, a toxin-mediated travellers diarrhea, or a *Clostridium* or a *C. perfringens* welchii or a *C. difficile* infection or a pseudo-membranous colitis associated with a *Clostridium* infection, or for preventing, decreasing or delaying the symptoms of, ameliorating stabilizing, or treating individuals (e.g., patients or animals) with spondyloarthropathy, spondylarthritis or sacrolileitis (an inflammation of one or both sacroiliac joints); a nephritis syndrome; an inflammatory or an autoimmune condition having a gut or an intestinal component such as lupus, irritable bowel syndrome (IBS or spastic colon) or a colitis such as Ulcerative Colitis or Crohn's Colitis; constipation, autism; degenerative neurological diseases such as amyotrophic lateral sclerosis (ALS), Multiple Sclerosis (MS) or Parkinson's Disease (PD); a Myoclonus Dystonia (e.g., Steinert's disease or proximal myotonic myopathy); an autoimmune disease such as Rheumatoid Arthritis (RA) or juvenile idiopathic arthritis (JIA); Chronic Fatigue Syndrome (including benign myalgic encephalomyelitis, chronic fatigue immune dysfunction syndrome, chronic infectious mononucleosis, epidemic myalgic encephalomyelitis); obesity; hypoglycemia, pre-diabetic syndrome, type I diabetes or type II diabetes; Idiopathic thrombocytopenic purpura (ITP); an acute or chronic allergic reaction such as hives, a rash, a urticaria or a chronic urticaria; and/or insomnia or chronic insomnia, Grand mal seizures or petit mal seizures, comprising:

administering to an individual in need thereof a delivery vehicle, formulation, pharmaceutical preparation, product of manufacture, container or device of the invention, or a product (article) of manufacture of the invention, in single, repeat or multiple administrations, deliveries or infusions.

In alternative embodiments, the amount of the entire (or substantially entire) microbiota, the treated or untreated fecal sample, or the partially, substantially or completely isolated or purified fecal flora, is formulated for or calibrated for repeat or multiple delivery or infusions; or the entire (or substantially entire) microbiota, the treated or untreated fecal sample or the partially, substantially or completely isolated or purified fecal flora is delivered in repeated or multiple infusions, wherein optionally the repeated or multiple administration, delivery, infusion or implantation protocol comprises infusions done daily for the first about 10 days, second daily for about 10 days, third daily then fourth daily possibly weekly and then optionally maintain second or more weekly infusions until the histology reverses towards normality.

In alternative embodiments, the invention provides devices for delivering a (bacterial flora-comprising) composition of the invention, or an entire (or substantially entire) microbiota or a fecal material comprising:

(a) a device as illustrated in FIG. 1 or FIG. 2, or equivalent thereof; or (b) (1) a bag or container comprising an exit aperture operably connected to the proximal end of a flexible tube or equivalent, wherein the bag or container is optionally made of a material impervious to a gas or to oxygen, and optionally the bag or container is made of a flexible material, or a polyethylene terephthalate polyester film-comprising (or a MYLAR™-comprising) material, and optionally the bag or container is an (IV-like) intravenous-like bag, and optionally the bag or container has an attachment that will allow the bag to be hung on a stand, e.g., to be positioned/hung above an endoscope, and optionally the bag or container is operably connected via an open or close valve or equivalent to a negative pressure device that can remove all gas or air from the bag, and optionally the bag or container is operably connected via an open or close valve or equivalent to a fluid source or storage container for flushing out the bag through the exit aperture, and optionally the fluid source or storage container is under positive pressure, and optionally the flexible tube or equivalent comprises at least one clip or close valve or one way valve to prevent backwash of material from distal to proximal portions of the tube, or from the tube back to the bag or container;

(2) an open or close valve or equivalent or an obdurator screwtop at the distal end of the flexible tube or equivalent, and optionally a Luer lock tip for attachment to a colonoscope or an endoscopic Luer lock port or equivalent, wherein optionally the Luer lock tip is built into the valve, or is separate from the valve, and optionally an enema tube tip for attachment to an enema tube or device or equivalent, wherein optionally the enema tube tip is built into the valve, or is separate from the valve, and optionally further comprising a safety device or safety clip to close the distal aperture in case the valve or Luer lock tip, or enema tip, is lost (flies off) under pressure; and (3) a pump, or a hand pump, for moving material in the bag or container through the flexible tube or equivalent and out the distal end or out the open or close valve or equivalent; or (c) the device of (a) or (b), further comprising a fecal material or a composition of the invention.

In alternative embodiments, the invention provides bags or containers comprising an entire (or substantially entire) microbiota, or a treated or untreated fecal flora, or a partially, substantially or completely isolated fecal flora, or a composition of the invention (e.g., a formulation comprising an entire (or substantially entire) microbiota, a partially, substantially or completely isolated or purified fecal flora, or a composition comprising a fecal flora substantially or completely purified of non-fecal floral fecal material), and optionally further comprising an excipient, or a fluid, a saline, a buffer, a buffering agent or a media, or a fluid-glucose-cellobiose agar (RGCA) media, wherein the bag or container is structurally the same as or similar to a bag or container of a device of the invention (e.g., as illustrated in FIG. 1 or FIG. 2), wherein optionally the interior of the bag is substantially or completely an oxygen-free environment, or the interior of the bag is substantially or completely similar to an anaerobic environment.

In alternative embodiments, specific anti *C. difficile* oral antibodies (for example avian) can be added to a solution (e.g., a saline, media, buffer) used to isolate or purify, store, freeze, freeze-dry, spray-dry lyophilize, transport, reconstitute and/or deliver a composition (e.g., a partially, substantially or completely isolated or purified fecal flora, or a composition comprising a fecal flora substantially or completely purified of non-fecal floral fecal material) of the invention. The combination of the product with these specific anti *C. difficile* oral antibodies enhances the eradication mechanism of the product.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

Like reference symbols in the various drawings indicate like elements. Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides compositions, e.g., formulations and pharmaceutical preparations, products of manufacture, and containers and delivery vehicles, and devices and delivery materials, comprising treated and/or isolated faecal (fecal) material for faecal floral transplantation. In one embodiment, the treated and/or isolated fecal material of the invention comprising faecal floral (e.g., bacteria) is transplanted between different individuals, e.g., human to human or between animals. In one embodiment, the treated fecal material of the invention is transplanted back into the same individual from which it was collected, e.g., to repopulate a colon after drug treatment (e.g., antibiotic treatment or chemotherapy) or after an orthostatic lavage, e.g., for inducing the purgation (e.g., cleansing) of a gastrointestinal (GI) tract, including a colon.

The invention provides methods for the amelioration, stabilization, or treatment of a bowel disease or infection comprising use of a delivery vehicle, formulation, product of manufacture, or container or device of the invention; e.g., as a fecal bacteriotherapy, fecal transfusion, fecal transplant, or human probiotic infusion (HPI). In alternative embodiments, the invention provides methods for ameliorating, stabilizing, treating or preventing any infection, bowel disease or condition having a bowel dysfunction component, for example, a poisoning, a pseudomembranous colitis, a *Clostridium difficile* infection, an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travellers' diarrhea, small intestinal bacterial overgrowth, chronic pancreatitis, or a pancreatic insufficiency.

For example, in one embodiment, as antibiotics do not eradicate *C. difficile* and its spore, a delivery vehicle, formulation, product of manufacture, or container or device of the invention comprising treated and/or isolated fecal flora can ameliorate, stabilize or eradicate *C. difficile* (or the pseudomembranous colitis associated with this infection) when infused into a colon of the infected or ill individual, e.g., a patient or animal. In alternative embodiments the fecal flora obtained from a donor (which in treated or isolated form is in alternative embodiments in a delivery vehicle, formulation, product of manufacture, or container or device of the invention) comprises a part of, substantially all of, or all of the infected or ill recipient's missing or inadequate (e.g., in numbers or function) fecal flora, e.g., bacteria. While the invention is not limited by any particular mechanism of action, in some embodiments it is the transfer of the equivalent of: a part of, substantially all of, or all of the fecal flora of the infected individual from the donor to the recipient (e.g., from human to human) that ameliorates or eradicates the infection or the pseudo-membranous colitis associated with this infection.

In alternative embodiments, the compositions, e.g., formulations and pharmaceutical preparations, and devices, delivery materials, delivery vehicles, products of manufacture, containers and devices of the invention allow the safe transplantation of fecal flora (e.g., human flora) components to individuals in need thereof, e.g., to infected, sick and dying patients, thus providing a consistently safe yet functioning flora for delivery to a recipient or patient.

In alternative embodiments, the invention provides a reliable method for producing standardized fresh fecal flora which can have a long shelf life. For example, in one embodiment, the delivery vehicle, formulation, pharmaceutical preparation, product of manufacture, container or device comprising the fecal flora comprises a substantially or completely oxygen-free environment. In another embodiment, nutrients such as "prebiotic nutrients" can be added (e.g., in dry or liquid forms) to a solution (e.g., a saline, media, buffer) used to isolate or purify, store, freeze, freeze-dry, spray-dry, lyophilize, transport, reconstitute and/or deliver a composition (e.g., a partially, substantially or completely isolated or purified fecal flora, or a composition comprising a fecal flora substantially or completely purified of non-fecal floral fecal material) of the invention. A prebiotic nutrient can be any ingredient that stimulates the stability, growth and/or activity of the fecal flora, e.g., bacteria; for example, in alternative embodiments, polyols, fructooligosaccharides (FOSs), oligofructoses, inulins, galactooligosaccharides (GOSs), xylooligosaccharides (XOSs), polydextroses, monosaccharides such as tagatose, and/or mannooligosaccharides are used as prebiotics to practice this invention. In one embodiment, the prebiotics are added to prevent "shock" to the fecal flora subsequent to their isolation or purification, freezing, freeze-drying, spray-drying, reconstitution in solution and the like.

In alternative embodiments, components of the compositions, e.g., delivery vehicles, formulations and pharmaceutical preparations, products of manufacture, or containers or devices, of the invention comprise an entire (or substantially entire) microbiota, or a *Bacteroides* and/or *Firmicutes* in large numbers (e.g., a larger proportion of *Bacteroides* and/or *Firmicutes* is present that is normally found in situ), e.g., to be able to ameliorate and/or eradicate a *C. difficile* infection and/or the pseudo-membranous colitis associated with this infection. In alternative embodiments, the compositions, e.g., delivery vehicles, formulations and pharmaceutical preparations, products of manufacture, or containers or devices, of the invention can be available (e.g., formulated and/or dosaged for) for recurrent use in individuals, e.g., in patients or animals, with the more difficult to treat conditions such as colitis (e.g., the pseudo-membranous colitis of a *C. difficile* infection) and constipation.

In alternative embodiments, components of the compositions e.g., delivery vehicles, formulations and pharmaceutical preparations, products of manufacture, or containers or devices, of the invention comprise a selection of bacterial species e.g. *Bacteroides, Firmicutes, Bacillus thuringiensis* (a bacterium capable of producing peptide antibiotics for *C. difficile*). The bacterial species may be separated by centrifugation or plasmapharesis.

In alternative embodiments the selection of bacterial species e.g. *Bacteroides, Firmicutes, Bacillus thuringiensis* may be added to components of the compositions e.g., delivery vehicles, formulations and pharmaceutical preparations, products of manufacture, or containers or devices as fortification of concentrations comprising the bacterial species to contain wild types of bacteria.

In alternative embodiments, compositions of the invention can be formulated as fecal slurries, saline or buffered suspensions (e.g., for an enema, suspended in a buffer or a saline), in a drink (e.g., a milk, yoghurt, a shake, a flavoured drink or equivalent) for oral delivery, and the like.

In alternative embodiments, compositions of the invention can be formulated as an enema product, a spray dried product, reconstituted enema, a small capsule product, a small capsule product suitable for administration to children, a bulb syringe, a bulb syringe suitable for a home enema with a saline addition, a powder product, a powder product in oxygen deprived sachets, a powder product in oxygen deprived sachets that can be added to, for example, a bulb syringe or enema, or a spray dried product in a device that can be attached to a container with an appropriate carrier medium such as yoghurt or milk and that can be directly incorporated and given as a dosing for example for children.

In one embodiment, compositions of the invention can be delivered directly in a carrier medium via a screw-top lid wherein the fecal material is suspended in the lid and released on twisting the lid straight into the carrier medium.

In alternative embodiments methods of delivery of compositions of the invention include use of fecal slurries into the bowel, via an enema suspended in saline or a buffer, orally in a drink (e.g., a milk, yoghurt, a flavoured drink and the like), via a small bowel infusion via a nasoduodenal tube, via a gastrostomy, or by using a colonoscope. In some embodiment, there may be advantages delivering via a colonoscope to infuse as proximally as possible, and to detect any colonic pathology.

In alternative embodiments methods, fecal flora used in the composition and methods of the invention is initially derived (entirely or in part) from an individual screened or tested for a disease or infection, and/or the fecal flora is initially derived from an individual screened to have a normal, healthy or normal, representative "wild type" population of fecal flora; e.g., a normal complement of a *Bacteroides* and/or *Firmicutes*, and/or other fecal flora such as *Bacillus Thuringiensis*. In one embodiment, depending on a deficiency of a floral (e.g., bacterial) specie or species in a donor fecal material, or to achieve a desired effect, one or more additional (or "supplemental") species, e.g., *Bacteroides, Firmicutes* and/or *Bacillus Thuringiensis* species, is added to (or is administered with) the delivered product either initially when the product is made, or at the time of delivery, e.g., the additional species is/are mixed in before application to the individual (e.g., patient or animal), e.g., when a powder, lyophilate, or freeze-dried composition is reconstituted for delivery; or the one or more additional (or "supplemental") species can be co-administered. These additional floral species can be directly isolated or purified from a donor, or can be expanded (cultured) for a time in vitro before addition, or can come from (be derived from) a pure culture, e.g., from an ATTC stock. For example, in some applications, e.g., to achieve a desired effect or therapeutic outcome, a delivery of an enhanced amount of one or more fecal flora (e.g., bacterial) species is used, e.g., the delivered product (e.g., an entire (or substantially entire) microbiota, or a composition comprising a complete or partial fecal flora, or a partially, substantially or completely isolated or purified fecal flora) is enhanced with (is "spiked" with") one or more additional (or "supplemental") species, e.g., *Bacteroides, Firmicutes* and/or *Bacillus Thuringiensis* species, which can be directly isolated from a donor, or can come from a pure culture, and the like.

In some embodiments, selection of the donor is of crucial importance, e.g., to avoid infecting the recipient with a separate infection or disease. In alternative embodiments the donor is tested (screened) at least for e.g., retrovirus (e.g., human immunodeficiency virus, HIV); hepatitis A, B, and/or C; cytomegalovirus; Epstein-Barr virus, detectable parasites and/or bacterial pathogens, depending on the specie of the donor and recipient, e.g., human or animal.

In alternative embodiments, the invention provides a process for preparing fecal flora (e.g., an entire (or substantially entire) microbiota) for transplantation, first comprising a collection from one or more healthy (e.g., screened) donor(s). In alternative embodiments, a fresh stool is transported via a stool collection device of the invention, which in one embodiment comprises a suitably oxygen free (or substantially oxygen free) appropriate container. An exemplary suitable stool collection device 1 is shown in FIG. 1A. FIG. 1A shows an exemplary container of the invention for containing the stool and including a slot 2 for receiving the stool. The container may then be placed into a bag 3 suitably a disposable leak proof ziplock/sealing bag.

In alternative embodiments, the container can be made oxygen free by e.g., incorporating into the container a built in or clipped-on oxygen-scavenging mechanism, e.g., oxygen scavenging pellets as described e.g., in U.S. Pat. No. 7,541,091. In another embodiment, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one embodiment, oxygen-scavenging polymers are used to make the container itself or to coat the container, or as pellets to be added; e.g., as described in U.S. Pat. App. Pub. 20110045222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one embodiment, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one embodiment, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

Alternatively, in addition to or in place of the oxygen-scavenging mechanism, the air in the container is replaced (completely or substantially) with nitrogen and/or other inert non-reactive gas or gases. In alternative embodiments, the container simulates (creates) partially, substantially or completely an anaerobic environment.

In alternative embodiments, the stool (e.g., fecal sample) is held in an aesthetically acceptable container that will not leak nor smell yet maintain an anaerobic environment. In alternative embodiments, the container is sterile before receiving the fecal flora.

In alternative embodiments, the container is maintained below room temperature, e.g., refrigerated, during most or all of its preparation, transportation and/or storage at e.g., a "stool bank" or at the site where the transplantation will take place. For example, once delivered to a "processing stool bank" it is stored in a cool room, cold container or ref ridgerator to minimize flora metabolism. In alternative embodiments, it is not to be frozen to prevent destruction of the bacterial cells of the stool.

In alternative embodiments, stabilizing agents such as glycerol are added to the harvested and/or stored material. In one embodiment, the stool is frozen suddenly in liquid nitrogen or any similar coolant so e.g., it can be stored for prolonged periods of time while waiting processing.

In alternative embodiments, the stool is tested for various pathogens, as noted above. In alternative embodiments, once cleared of infective agents, it is homogenized and filtered to remove large particles of matter. In alternative embodiments, it is subdivided into desired volumes, e.g., which can be between 5 cc and 3 or more liters. For example, in one embodiment, a container comprises a 50 gram (g) stool, which can be held in an appropriate oxygen resistant plastic, e.g., a metallized polyethylene terephthalate polyester film, or a metallized MYLARN.

In alternative embodiments, as shown in FIG. 1B, the exemplary therapeutic vehicle (delivery system) 10 and the equipment in which the stool material is held is an intravenous-like (IV-like) giving set 11, e.g., with a hand pump 12 attached to the set. Suitably the bag 11 is metallised MYLARN which is impervious to gases. The hand pump 12 can allow the contents of the liquefied stool residing in the upper part of the plastic device to be easily pumped forward when the entire equipment tubing is attached by Luer lock mechanism 13 to the colonoscope biopsy channel. In this way a colonoscope or even an enteroscope will become the delivery mechanism. For this embodiment, this would usually be into the colon at any distance, and alternatively into the caecum. In alternative embodiments, the material is passed into a terminal ileum or even higher, as desired. In alternative embodiments, it can be infused into the duodenum or below with an enteroscope. In alternative embodiments, C. difficile (or the pseudo-membranous colitis associated with this infection) is ameliorated or eradicated with the infused fecal sample, or treated stool.

Another alternative embodiment is shown in FIG. 2. In this embodiment the therapeutic vehicle/delivery system 20 including an IV-like bag 21 including saline (NaCl) 22 and stool/cells 23 of the invention. In addition to the hand pump 24 and Luer lock 25, the delivery system is provided with a flushing port 26 (for flushing out the bag), a clip 27 (to prevent backwash) and an enema tip 28 with Luer lock attachment.

In alternative embodiments, the transplant material is subject to homogenization and straining. In alternative embodiments, this treated material is placed into a container, e.g., a bag, that can be attached to a nasogastric or naso-duodenal tube to allow the contents to be infused e.g., into either a stomach, duodenum or the distal jejunum. Alternatively it can be kept in a container, e.g., a bag, which can be attached to an enema tip to be given as an enema.

In alternative embodiments, to separate the non-bacterial components and produce a stable product that can be frozen or lyophilized and have a long shelf life, the stool can be homogenized and filtered from rough particulate matter. In alternative embodiments, the microscopic fiber/nonliving matter is then separated from the bacteria. Several methods can be used, including e.g., recurrent filtration with filter sizes, e.g., coming down to the size of the bacterium.

In one embodiment different filters are used to isolate the bacterial spp. This differs from the technique used for example by Williams in WO 2011/033310A1 which uses a crude technique of filtration with a gauze and is inferior to that of the present invention which utilises different sized filtration membranes to obtain the purified bacteria.

In one embodiment, a filtration procedure for filtering whole stool is suitably used to reach the highest concentration of almost 100% bacteria. In one embodiment, the filtering procedure is a two-step procedure suitably using glass fibre depth fillers for initial clarification. In one embodiment, the stool is filtered under positive pressure. In one embodiment, this would be using a combination or sandwich configuration with a 30 micron PVDF filter. In one embodiment, this sandwich procedure will be filtering the product under positive pressure. Later, membrane concentration can, in one embodiment, be used as another step to reduce the volume of the filtrate. In one embodiment, this can be done prior to freeze drying or spray drying under nitrogen cover.

Alternative membranes that can be used for filtration include, but not limited to, nylon filters, cellulose nitrate filters, PES filters, Teflon filters, mixed cellulose Ester filters, polycarbonate filters, polypropylene filters, PVC filters or quartz filters. Various combinations of these can be used to achieve a high purity of bacteria with solids and liquid removed ready for freezing, spray-drying or lyophilisation.

For freezing, in alternative embodiments, the bacteria is held in a liquid that will prevent bursting of cells on thawing. This can include various stabilizers, e.g., glycerol and appropriate buffers, and/or ethylene glycol. In alternative embodiments, cryo-protectance uses final concentrations of stabilizer(s) of between about 20% to 60%, depending in the stabilizer(s) used; this helps stabilize proteins by preventing formation of ice crystals that would otherwise destroy protein structures.

In alternative embodiments, stabilizers that help reduce destruction of living bacteria include skim milk, erythritol, arabitol, sorbitol, glucose, fructose and other polyols. Polymers such as dextran and polyethylene glycol can also be used to stabilize the faecal bacterial cells.

Mixing the appropriate amount of the bacterial flora with the stabilizer allows it to be snap frozen and kept frozen in the container that will be used to transport it to appropriate facility where the patient will have this infused after thawing.

In alternative embodiments, an entire (or substantially entire) microbiota, or an isolated and/or treated (e.g., purified or isolated) fecal material and/or flora, can be lyophilized or freeze dried, or the product can be frozen. In alternative embodiments freeze-drying allows the majority of cells to remain viable, and produces a powdered form of the product that can be gently pulverized into a powder. The powder, or lyophilized or freeze-dried flora or isolate, then can be encapsulated into a carrier, e.g., a tablet, geltab, pill or capsule, e.g., an enteric-coated capsule, or placed into oil-filled capsules for ingestion. Alternatively, the freeze-dried or lyophilized product, or powder, can be reconstituted before delivery to an individual in e.g., a fluid, e.g., a sterile fluid, such as saline, a buffer or a media such as a fluid-glucose-cellobiose agar (RGCA) media.

In alternative embodiments an entire (or substantially entire) microbiota, or an isolated and/or treated (e.g., purified or isolated) fecal material and/or flora can be spray-dried. In one embodiment spray-drying is preferred over freeze-drying or lyophilising., In alternative embodiments, the entire (or substantially entire) microbiota, or isolated and/or treated fecal material and/or flora, is supplemented with wild type bacteria which has been derived from normal animal (e.g., human) flora and/or recombinantly treated bacteria, e.g., recombinant microorganisms that can synthesize a protein, small molecule or carbohydrate that has a self-protective or ameliorative effect; or recombinant microorganisms that can self-destruct when provided with an appropriate signal, e.g., a chemical delivered by ingestion.

In alternative embodiments, the transplantation product (e.g., a composition of the invention comprising an isolated or purified fecal flora or an entire (or substantially entire) microbiota) is delivered by an infusion, e.g., through the rectum, stoma or down the upper gastrointestinal (GI) tract, or it can be used in a suppository pill, tablet or encapsulated form, e.g., with an enteric-coated graded release capsule or a tablet, e.g., with the addition of excipients. In alternative embodiments the transplantation product is administered as a suppository to give the highest concentration in the rectum.

In one embodiment, the transplantation product (e.g., a composition of the invention comprising an isolated or purified fecal flora or an entire (or substantially entire) microbiota) is stored before, during and/or after delivery to an individual, or for or during the delivery, in a fluid, e.g., a sterile fluid, such as saline, a buffer or a media such as a fluid-glucose-cellobiose agar (RGCA) media.

In alternative embodiments, the compositions and methods of the invention are used to ameliorate, stabilize, prevent and/or treat: various gastrointestinal conditions, e.g., *C. difficile* infection, *C. perfringens* welchii and other *Clostridium* infections, irritable bowel syndrome, constipation, pouchitis, Crohn's disease and microscopic colitis; neurological conditions such as Parkinson's disease, myoclonus dystonia, autism, amyotrophic lateral sclerosis and multiple sclerosis, Grand mal seizures or petit mal seizures. In one embodiment, the neurological conditions are treated by encapsulated or frozen material. In alternative embodiments, for colitis patients, recurrent administration is required to suppress and reverse the inflammatory bowel disease and irritable bowel syndrome.

In alternative embodiments, a crude collected stool is filtered and/or homogenized, and then its bacterial cells are separated (e.g., from the "crud" which contains the fiber) by plasmapheresis, centrifugation, celltrifuge, column chromatography (e.g., affinity chromatography), immunoprecipitation (e.g., antibodies fixed to a solid surface, such as beads or a plate). Centrifugation, including use of a "celltrifuge" (e.g., a Baxter model MEDIFUGE I2I5™) are processes that involve centrifugal force to separate mixtures. For "centrifugation", the densest components will then fly to the outside of the spinning plates while the rest of the components will migrate to the axis. The effect of the gravitational force will be increased by spinning the flattened product between rapidly moving glass plates. The centrifuge or celltrifuge can be set up such that the stool will be diluted adequately and set on a spinning cycle and collection of cells will occur only peripherally on the centrifuge.

In alternative embodiments, wild type bacterial cells (including e.g., an entire (or substantially entire) microbiota) separated or purified e.g., by centrifugation, celltrifugation, plasmapheresis and the like, are frozen using a cryoprotectant. In alternative embodiments, this material is frozen in a container, e.g., a bag, which can then be used to infuse through a colonoscope, naso-duodenal or nasogastric tube. In alternative embodiments, it can be delivered to a facility (e.g., a hospital pharmacy) to be kept frozen, e.g., at −20° C. or below. Alternatively the centrifuged material can be lyophilized; and can be used either in a solution, gels, geltabs, pills, capsules or tablets, or suppositories, e.g., to be reconstituted later as an enema or infuse set through a colonoscope.

In one embodiment the cryoprotectant is trehalose. Trehalose may also function as a component upon reconstitution or as an additional agent prior to spray-drying or freeze-drying.

In alternative embodiments, solutions, gels, geltabs, pills, capsules or tablets comprising compositions of the invention (e.g., isolated or purified fecal flora or an entire (or substantially entire) microbiota) can be taken long term, e.g., on a daily basis long term, e.g., for one, two, three or four weeks or months or more, to treat, stabilize, ameliorate or prevent a chronic and/or an immune condition such as e.g., persistent infection, rheumatoid arthritis, systemic lupus erythematosus, autoimmune renal diseases, e.g., nephritis, severe obstruction, inflammatory bowel disease (IBD), irritable bowel syndrome (IBS), and other conditions set forth herein.

Preparations or Cultures of Entire Microbiota

In alternative embodiments, compositions (e.g., products of manufacture or formulations) of the invention, comprise preparations, formulations, cultures or culture extracts or isolates comprising an entire or substantially entire microbiota of an individual or specie, e.g., a human or other mammal. In alternative embodiments, the invention provides compositions and methods for preventing, decreasing the symptoms of, ameliorating stabilizing, or treating various infections, disease or conditions comprising administration of these "entire or substantially entire microbiota" preparations (e.g., cultures or culture isolates); for example, administering "entire or substantially entire microbiota" preparations for preventing, decreasing the symptoms of, ameliorating, stabilizing, or treating: spondyloarthropathy, spondylarthritis or sacrolileitis (an inflammation of one or both sacroiliac joints); a nephritis syndrome; an inflammatory or an autoimmune condition having a gut or an intestinal component such as lupus, irritable bowel syndrome (IBS or spastic colon) or a colitis such as Ulcerative Colitis or Crohn's Colitis; constipation, autism; a degenerative neurological diseases such as amyotrophic lateral sclerosis (ALS), Multiple Sclerosis (MS) or Parkinson's Disease (PD); a Myoclonus Dystonia (e.g., Steinert's disease or proximal myotonic myopathy); an autoimmune disease such as Rheumatoid Arthritis (RA) or juvenile idiopathic arthritis (JIA); Chronic Fatigue Syndrome (including benign myalgic encephalomyelitis, chronic fatigue immune dysfunction syndrome, chronic infectious mononucleosis, epidemic myalgic encephalomyelitis); obesity; hypoglycemia, pre-diabetic syndrome, type I diabetes or type II diabetes; Idiopathic thrombocytopenic purpura (ITP); an acute or chronic allergic reaction such as hives, a rash, a urticaria or a chronic urticaria; and/or insomnia or chronic insomnia, Grand mal seizures or petit mal seizures.

In alternative embodiments, the invention provides compositions and methods for administration of these "entire or substantially entire microbiota" preparations to prevent, decrease the symptoms of, ameliorate or treat various infections, diseases or conditions comprising e.g., constipation, an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, a pancreatic insufficiency, exposure to a poison or a toxin or for an infection, a toxin-mediated travelers diarrhea, a poisoning, a pseudomembranous colitis, a *Clostridium* infection, a *C. perfringens* welchii or a *Clostridium difficile* infection, a neurological condition, Parkinson's disease, myoclonus dystonia, autism, amyotrophic lateral sclerosis or multiple sclerosis, Grand mal seizures or petit mal seizures.

While the invention is not limited by any particular mechanism of action, a treated or untreated fecal sample of the invention, or a composition comprising a complete or partial fecal floral sample (e.g., an entire or substantially entire microbiota') of the invention, or a partially, substantially or completely isolated or purified fecal flora of the invention, when infused into a recipient (e.g., a human or a mammal) colonize the gut. In one embodiment, these fecal floral preparations are made (e.g., isolated) by filtering human flora, and/or by spinning or centrifuging, plasmapheresis, celltrifuge, column chromatography (e.g., affinity chromatography), or immunoprecipitation and the like, to extract almost pure or substantially pure, or pure, fecal flora (e.g., "bacterial mass").

In an alternative embodiment, compositions of the invention are prepared by culturing an entire (or substantially entire) microbiota cultured simultaneously (e.g., all together without any pre-segregating out of any particular bacterial species). In one embodiment, an "entire (or substantially entire) microbiota culture" sample is formulated e.g., as a liquid, or as a freeze dried or frozen product. In one embodiment, these preparations do not contain any (or are substantially free of) non-floral material, e.g., non-absorbed components normally present in a fecal sample, e.g., a raw human stool. In one embodiment, a raw (e.g., human) stool is made into a therapeutic agent or formulation.

In one embodiment, the invention provides methods of culturing an entire mammalian, e.g., a human, flora by taking a stool sample from a suitable donor. In one embodiment, a suitable donor is a pathogen free individual; e.g., in one aspect a sample is collected from a donor who has been classified as normal and free of any pathogens. In one embodiment, as a stand-alone therapeutic or in conjunction with other therapies, bacteria from lean donors may be used to treat obesity in obese patients.

In alternative embodiments, a culture is carried out for about 2, 3, 4, 5, 6, 7 or 8 or more days under total or substantially total anaerobic conditions. Standard culturing procedures can be used using, e.g., a non-selective gut microbiota medium (GMM), and in one embodiment, incubated at (human) body temperature of about 36.8° C. An atmosphere devoid of (or substantially devoid of) oxygen and containing nitrogen, carbon dioxide and hydrogen can be used. Differing GMM can be used with varying concentrations of the composition of the GMM.

Colonies or the cultured flora are then harvested by e.g., scraping with a sterile scraper. Harvested colonies or cultured flora can be frozen e.g., in about minus 80° or below (e.g., in a freezer), using e.g., a cryoprecipitate such as e.g., a glycerol, a cysteine or a milk. Such cultures can then be aliquoted to be used only once (as re-culturing can cause a loss of adhesions). In one embodiment, methods can comprise re-culturing e.g., in a lipid culture medium resembling a GMM. This entire medium can be frozen again using e.g., a glycerol with a cysteine; and in one embodiment, can be kept frozen or freeze-dried. This can produce between about 108 to about $10^{10}$ CFUs.

In alternative embodiments, powder, dried, frozen, freeze-dried or liquid or other forms of the cultured (e.g., human) bacteria (e.g., an entire or substantially entire microbiota") can be formulated and/or used either as an enema, a food or food supplement or formulation (e.g., added to a yoghurt, milk, drink, flavoured drink or a food), or delivered as a capsule, tablet, geltab or the like (e.g., as an enteric coated capsule) to recolonise or alternatively or therapeutically "colonize" a gut flora.

In alternative embodiments cultured bacteria is added to the culture or sample or formulation of "entire (or substantially entire) microbiota". For example, in one embodiment the first administration or the initial daily formulations comprise only an "entire microbiota" formulation; while in other embodiments the first administration or the initial daily formulations comprise both "entire microbiota" and additional cultured bacteria, e.g., cultured probiotic bacteria. In alternative embodiments, the less frequent formulations or dosages (which can be stepwise in small or larger intervals, or periodic intervals, or intervals as determined by the physician or veterinarian according to rate of improvement, and the like) comprise only "entire microbiota"; while in other embodiments comprise both "entire microbiota" and the additional cultured bacteria, e.g., cultured probiotic bacteria.

In alternative embodiments, to achieve a desired effect or therapeutic outcome, the additional cultured bacteria (e.g., added to the "entire microbiota") is a *Bacteroides, Firmicutes* and/or *Bacillus thuringiensis* species, which be directly isolated from a donor, or can come from a pure culture, and the like. In alternative embodiments, a delivery of an enhanced amount of one or more fecal flora (e.g., bacterial) species is used, e.g., the delivered "entire microbiota" product is enhanced with (is "spiked" with") one or more additional species, e.g., a *Bacteroides, Firmicutes* and/or *Bacillus thuringiensis* species.

Multiple or Repeated Infusions or Administrations

In alternative embodiments, compositions (e.g., products of manufacture or formulations) of the invention, including a treated or untreated fecal sample, or a partially, substantially or completely isolated or purified fecal flora, or a "culture of entire human microbiota" of the invention, or an entire (or substantially entire) microbiota or combination thereof is formulated for or calibrated for repeat or multiple delivery or infusions. In alternative embodiments of methods of the invention, the partially, substantially or completely isolated or purified fecal flora, e.g., of entire human microbiota, or an entire (or substantively entire) microbiota, or combination thereof, are delivered or administered by repeat or multiple delivery or infusions.

The invention thus provides compositions and methods for treating, stabilizing, or ameliorating gut flora infections or conditions which are difficult to permanently reverse, or for treating or ameliorating conditions characterised by gut flora infections which are difficult to permanently reverse. It has been discovered that multiple, repeated infusions can overcome gut flora infections or conditions that are difficult to permanently reverse. In alternative embodiments, in practicing the methods and/or compositions (e.g., products of manufacture or formulations) of the invention, multiple or repeated fecal flora implantations (administrations, infusions) can overcome an underlying tenacious ongoing flora infection in an individual (e.g., an animal or a patient) with e.g., pathogenic and/or foreign bacterial strains, or a chronic condition.

With inadequate elimination of the infective (e.g., pathogenic and/or foreign) bacteria, the ongoing original symptoms can return. It is known that bacteria sometimes do not divide and may live in biofilms in many wet (e.g., interior) surfaces of the body. Secondly, bacteria have spores which can be more difficult to eradicate at intermittent times of sporulation. There are also dormant forms of bacteria that can be intra- and extra-cellular where they are much more difficult to eradicate—unless the dormant form is dividing. Finally, intracellular bacteria may wait until the gut wall cell in which they are housed is shed into the gut lumen re-infecting the flora. In alternative embodiments, the multiple or repeated bowel flora infusions of the methods of the invention can, and may be required, to kill or otherwise inactivate the viable (e.g., infective, pathogenic and/or foreign) bacteria which were protected inside the cell, biofilm and the like. In alternative embodiments, the multiple or repeated bowel flora infusions of the methods of the invention can, and may be required, to kill or otherwise inactivate bacterial cells that travel up crypts closer to lumen, where they are shed into the faecal stream and re-infect the individual or patient.

Additionally, in alternative embodiments, the multiple (recurrent) or repeated fecal flora implantations (administrations, infusions) of methods and/or compositions (e.g., products of manufacture or formulations) of the invention are effective for preventing, stabilizing, decreasing the symptoms of, ameliorating or treating individuals (e.g., patients) with: spondyloarthropathy, spondylarthritis or sacrolileitis (an inflammation of one or both sacroiliac joints); a nephritis syndrome; an inflammatory or an autoimmune condition having a gut or an intestinal component such as lupus, Irritable Bowel Syndrome (IBS or spastic colon) or a colitis such as Ulcerative Colitis or Crohn's Colitis; constipation, autism; a degenerative neurological diseases such as amyotrophic lateral sclerosis (ALS), Multiple Sclerosis (MS) or Parkinson's Disease (PD); a Myoclonus Dystonia (e.g., Steinert's disease or proximal myotonic myopathy); an autoimmune disease such as Rheumatoid Arthritis (RA) or juvenile idiopathic arthritis (JIA); Chronic Fatigue Syndrome (including benign myalgic encephalomyelitis, chronic fatigue immune dysfunction syndrome, chronic infectious mononucleosis, epidemic myalgic encephalomyelitis); obesity; hypoglycemia, pre-diabetic syndrome, type I diabetes or type II diabetes; Idiopathic thrombocytopenic purpura (ITP); an acute or chronic allergic reaction such as hives, a rash, a urticaria or a chronic urticaria; and/or insomnia or chronic insomnia, Grand mal seizures or petit mal seizures.

In alternative embodiments the invention is practiced (is carried out) either by use of methods or compositions of the invention, including recurrent enemas of human filtered stool, recurrent infusions through a naso-duodenal (ND) or a naso-gastric (NG) tube.

In alternative embodiments, methods or compositions of the invention formulate or use various formulations, e.g., frozen extracted stool bacterial material can be suspended as a flavoured drink or put down an ND or an NG tube or inserted as an enema.

In alternative embodiments, extracted bacteria—the 'wild types' are freeze-dried (optionally, after partial, substantial or complete purification and isolation) and formed into powder; they then can be ingested, e.g., as enteric-coated capsules, tablets, solutions and the like.

In alternative embodiments, these 'products' of the invention are initially taken, infused or administered daily, then less and less frequently, and in some embodiments, ultimately once every few weeks or monthly.

In alternative embodiments cultured bacteria can be used in addition to or with the partial, substantial or completely purified or isolated fecal flora. For example, in one embodiment the first administration or the initial daily formulations comprise only partial, substantial or completely purified or isolated fecal flora; while in other embodiments the first administration or the initial daily formulations comprise both partial, substantial or completely purified or isolated fecal flora and cultured bacteria, e.g., cultured probiotic bacteria. In alternative embodiments, the less frequent formulations or dosages (which can be stepwise in small or larger intervals, or periodic intervals, or intervals as determined by the physician or veterinarian according to rate of improvement, and the like) comprise only partial, substantial or completely purified or isolated fecal flora; while in other embodiments comprise both partial, substantial or completely purified or isolated fecal flora and cultured bacteria; or in other embodiments comprise only cultured bacteria, e.g., cultured probiotic bacteria.

In alternative embodiments, to achieve a desired effect or therapeutic outcome, the cultured bacteria is a *Bacteroides* and/or *Firmicutes* species and/or *Bacillus thuringiensis*, which may be directly isolated from a donor, or can come from a pure culture, and the like. In alternative embodiments, a delivery of an enhanced amount of one or more fecal flora (e.g., bacterial) species is used, e.g., the delivered product is enhanced with (is "spiked" with") one or more additional species, e.g., a *Bacteroides* and/or *Firmicutes* species and/or *Bacillus thuringiensis.*

In alternative embodiments, for adequate efficacy as to be determined by the skilled artisan, the formulations are introduced daily, or not daily—but instead recurrently for prolonged periods of time, e.g., in much higher doses. In alternative embodiments, the repeated or multiple infusion, administration or implantation protocols comprise infusions done daily for about the first 10 days, and subsequently a second daily different dosage or formulation for about 10 days, and optionally a subsequent different third daily; then optionally a different fourth daily, weekly, or monthly dosage or formulation, and then optionally maintaining different dosages or formulations for a further daily, weekly or monthly delivery or infusion until the histology reverses towards normality or other treatment parameter or goal is achieved; e.g., for the treatment of Irritable Bowel Syndrome, colitis such as Ulcerative Colitis or Crohn's Colitis, constipation, autism, degenerative neurological diseases such as Multiple Sclerosis (MS), Parkinson's Disease (PD), Myoclonus Dystonia, Rheumatoid Arthritis, Chronic Fatigue Syndrome, obesity, diabetes, type II diabetes, Idiopathic thrombocytopenic purpura (ITP), autoimmune diseases, chronic urticaria and/or insomnia or chronic insomnia, Grand mal seizures or petit mal seizures.

In alternative embodiments, the repeated or multiple infusion, administration or implantations are done with: a first formulation daily for the first 1, 2, 3, 4, 5, 6, 7, 8, 9, 10, 11, 12, 13, 14, or 15 days; a second dosage or formulation daily for a subsequent 1, 2, 3, 4, 5, 6, 7, 8, 9, 10, 11, 12, 13, 14, or 15 days or more; then optionally a third subsequent dosage or formulation daily (e.g., for a subsequent 1, 2, 3, 4, 5, 6, 7, 8, 9, 10, 11, 12, 13, 14, or 15 days or more); then optionally a fourth dosage or formulation daily or weekly (e.g., for a subsequent 1, 2, 3, 4, 5, 6, 7, 8, 9, 10, 11, 12, 13, 14, or 15 days, weeks, months or more); and optionally then maintaining weekly or monthly infusions until e.g., the histology reverses towards normality, or other appropriate parameter for treatment or recovery; e.g., for treatment of Irritable Bowel Syndrome, colitis such as Ulcerative Colitis or Crohn's Colitis, constipation, autism, degenerative neurological diseases such as Multiple Sclerosis (MS), Parkinson's Disease (PD), Myoclonus Dystonia, Rheumatoid Arthritis, Chronic Fatigue Syndrome, obesity, diabetes, type II diabetes, Idiopathic thrombocytopenic purpura (ITP), autoimmune diseases, chronic urticaria and/or insomnia or chronic insomnia, Grand mal seizures or petit mal seizures. One of skill in the art, e.g., a physician or veterinarian, can assess the individual's improvement and determine the exact, appropriate dosage or frequency of administration in this "repeat administration" embodiment of the invention.

In alternative embodiments, these exemplary protocols also can be used for infusing or ingesting cultured probiotic bacteria that would be swept down the bowel in waves so as to address the issue of the biofilms spores, dormant forms and intracellular bacteria.

In summary, in alternative embodiments, the invention provides compositions and methods for treating, stabilizing, or ameliorating gut flora infections that are difficult to permanently reverse, or for treating or ameliorating conditions characterised by or related to gut flora infections that are difficult to permanently reverse or control, by multiple, repeated infusions of fecal flora, as described herein. In alternative embodiments the fecal microbiota transplant compositions and methods of the invention are effective in the more difficult conditions listed above in addition to conditions where a *Clostridium*, e.g., *C. difficile*, is the infective agent. In alternative embodiments, repeated or recurrent infusions are the key to obtaining a cure, a stabilization or a prolonged remission.

Devices for Delivering Compositions of the Invention

The invention also provides devices for delivering compositions of the invention, e.g., an exemplary delivery device is illustrated in FIG. 1B. In alternative embodiments, a device of the invention also can comprise or consist of:

(b) (1) a bag or container comprising an exit aperture operably connected to the proximal end of a flexible tube or equivalent, wherein the bag or container is optionally made of a material impervious to a gas or to oxygen, and optionally the bag or container is made of a flexible material, or a polyethylene terephthalate polyester film-comprising (or a MYLAR™-comprising) material, and optionally the bag or container is an (IV-like) intravenous-like bag, and optionally the bag or container has an attachment that will allow the bag to be hung on a stand, e.g., to be positioned/hung above an endoscope, and optionally the bag or container is operably connected via an open or close valve or equivalent to a negative pressure device that can remove all gas or air from the bag, and optionally the bag or container is operably connected via an open or close valve or equivalent to a fluid source or storage container for flushing out the bag through the exit aperture, and optionally the fluid source or storage container is under positive pressure, and optionally the flexible tube or equivalent comprises at least one clip or close 25 valve or one way valve to prevent backwash of material from distal to proximal portions of the tube, or from the tube back to the bag or container;

(2) an open or close valve or equivalent or an obdurator screwtop at the distal end of the flexible tube or equivalent, and optionally a Luer lock tip for attachment to a colonoscope or an endoscopic Luer lock port or equivalent, wherein optionally the Luer lock tip is built into the valve, or is separate from the valve, and optionally an enema tube tip for attachment to an enema tube or device or equivalent, wherein optionally the enema tube tip is built into the valve, or is separate from the valve, and optionally further comprising a safety device or safety clip to close the distal 5 aperture in case the valve or Luer lock tip, or enema tip, is lost (flies off) under pressure; and (3) a pump, or a hand pump, for moving material in the bag or container through the flexible tube or equivalent and out the distal end or out the open or close valve or equivalent.

In alternative embodiments, a device of the invention further comprises a treated or untreated fecal flora, or a partially, substantially or completely isolated fecal flora, or a composition of the invention, e.g., a partially, substantially or completely isolated or purified fecal flora, or a composition comprising a fecal flora substantially or completely purified of non-fecal floral fecal material, and optionally further comprising an excipient, or a fluid, a saline, a buffer, a buffering agent or a media, or a fluid-glucose-cellobiose agar (RGCA) media.

In one embodiment, the invention provides a bag or container comprising a treated or untreated fecal flora, or a partially, substantially or completely isolated fecal flora, or a composition of the invention, e.g., a partially, substantially or completely isolated or purified fecal flora, or a composition comprising a fecal flora substantially or completely purified of non-fecal floral fecal material, and optionally further comprising an excipient, or a fluid, a saline, a buffer, a buffering agent or a media, or a fluid-glucose-cellobiose agar (RGCA) media, wherein the bag or container is structurally the same as or similar to a bag or container of a device of the invention, e.g., a bag or container comprising an exit aperture operably connected to the proximal end of a flexible tube or equivalent, etc., as described herein.

The invention will be further described with reference to the following examples; however, it is to be understood that the invention is not limited to such examples.

EXAMPLES

Example 1

Exemplary Methods of the Invention

One exemplary procedure of the invention involves a 5- to 10-day treatment with enemas comprising a treated or isolated fecal bacterial flora of the invention initially derived from a healthy donor. Alternatively, patients can recover after just one treatment.

In one embodiment, the best choice for donor is a close relative who has been tested for a wide array of bacterial and parasitic agents. The enemas are prepared and administered in a hospital environment to ensure all necessary precautions. An exemplary probiotic infusion of the invention can also be administered through a nasogastric tube, delivering the bacteria directly to the small intestine. These two methods can be combined to achieve a desired result. Regular checkups should be required up to a year following the procedure.

In one embodiment an autologous fecal sample is provided by a patient before a medical treatment, and it is stored in a refrigerator, lyophilized or freeze-dried or equivalent. Should the patient subsequently develop an infection, e.g., a *C. difficile* infection, the sample is prepared (extracted) with saline and filtered. The filtrate can be freeze-dried and the resulting solid enclosed in a capsule, e.g., an enteric coated capsule. Administration of the capsules can restore the patient's own colonic flora and combat the infection, e.g., the *C. difficile*. In one embodiment, samples are delivered into the duodenum via a nasal probe.

In one embodiment, a method of the invention comprises the collection from healthy donors of fresh, human flora (stool), bringing it to a centralized institution, processing it in such a fashion that it will be given prolonged life, checking for pathogens, maintaining temperature control to reduce metabolic activity of the bacteria and controlling for oxygen-shock, developing a storage facility of the homogenized, standardized flora, and shipping the flora out to distant hospitals to treat patients with e.g. acute pseudo membranous colitis, severe *C. difficile* infection, septicaemia or other comparable conditions.

In one embodiment, the product of the invention is a modified stool composition. The stool needs to be collected and promptly placed into an anaerobic container which extracts air, possibly with substances that adsorb and absorb oxygen or can be evacuated and filled with nitrogen or other gas which is either inert or will not damage anaerobic flora. It has to be held in an aesthetically acceptable container which will not leak the stool nor the gas which is producing the anaerobic situation. Once delivered to the central 'bank' the stool can be stored in a cold room to slow down metabolism but not be frozen to prevent the water expansion-destruction of the bacterial cells contained in stool.

In one embodiment, either antioxidants and/or substances such as glycerol are added to help stabilize the bacteria in the cold and prevent them from becoming destroyed during storage and during transport.

In one embodiment the product is stored/contained as (in) a volume of between about 10 cc and 3 liters of stool. In one embodiment it is stored in a (as a) 300 cc container (or amount) and held in appropriate oxygen-resistant material, e.g., a plastic, an oxygen-resistant or gas impervious polyethylene terephthalate polyester film (e.g., in metallized form), or a metallized MYLAR™, or an aluminized MYLAR™, which can be attached to a pump through a giving set that will be attached to the colonoscope and administered through a colonoscope into a distal small bowel or into the upper colon/terminal ileum, to overcome *Clostridium difficile* infection.

Central Flora Supply Institution or "Bank"

In one embodiment, an institution functions to supply the human flora in the following manner:

1. Stool will be collected in special containers and held cool anaerobically until it arrives at the central flora processing unit.

2. In a processing unit special additives will be added including glycerol, possibly antioxidants and other special preservatives and kept cool, homogenized and dispensed into appropriate intravenous-like bags but with somewhat thicker product such as a gas impervious polyethylene terephthalate polyester film, or an aluminized MYLAR™. This will prevent oxygen being transferred, nitrogen escaping and the smell being detected by administering staff. The bags will then be kept stored at a temperature that does not allow bacteria to freeze and be ready for transport in coolers to hospitals that will be carrying out the faecal transplantation.

3. The bag will be supplied with an attached giving set, so that it does not have to be handled by hospital staff. There will be attached to it a 'blood type' pump, with one way valve. On the (IV-like) intravenous-like bag there will be attachments that will be able to allow the bag to be hung on an IV fluids stand and be positioned/hung above the endoscope. The endoscopist will then take off the obdurator screwtop and attach to the Luer lock tip onto the endoscopic Luer lock port to be infused through the biopsy forceps channel at the tip of the colonoscope or endoscope. A safety device would be attached in case the tip flies off under pressure. The air will then be bled from the tube as the product is allowed to run down the 'giving set' with pressure mechanisms along the giving set, with air bled, and then stool only will be administered using the administering pump into the patient's colon and flushed, for example with some saline.

4. The endoscopist would then withdraw the colonoscope, turn the patient 'head down/legs up' to allow air and liquid to be absorbed and prevent the patient from undergoing defecation too early. This will allow the bacteria to re-gain temperature, start attaching themselves to the bowel wall as described e.g., by Grehan et al: J of Clinical Gastroenterology, September 2010.

A number of embodiments of the invention have been described. Nevertheless, it will be understood that various modifications may be made without departing from the spit and scope of the invention. Accordingly, other embodiments are within the scope of the following claims.

The invention claimed is:

1. An oxygen-free or substantially oxygen-free pharmaceutical preparation, comprising:
  (a) a formulation comprising:
    (i) a frozen, freeze-dried, spray-dried, lyophilized or powdered entire or at least 90% anaerobic microorganism population of a complete microbiota of a fecal sample; or
    (ii) all or at least 90% anaerobic microorganism population of a complete microbiota of a fecal sample in an excipient, a saline, a buffer, a buffering agent or medium, or a fluid-glucose-cellobiose agar (RGCA) medium, (b) an oxygen scavenging material, and
(c) an air tight or an anaerobic container,
wherein the pharmaceutical preparation provides an at least about 99.5% oxygen-free or oxygen-free containment or storage of the anaerobic microorganism population of (a)(i) or (a)(ii) in the air tight or the anaerobic container.

2. The pharmaceutical preparation of claim 1, wherein the anaerobic microorganism population of (a)(i) or (a)(ii) comprise a human anaerobic fecal flora.

3. The pharmaceutical preparation of claim 1, having contained therein a built-in or a clipped-on oxygen-scavenging mechanism.

4. The pharmaceutical preparation of claim 1, wherein the pharmaceutical preparation or the air tight or anaerobic container is coated with an oxygen scavenging material.

5. The pharmaceutical preparation of claim 1, wherein the pharmaceutical preparation or the air tight or anaerobic container comprises an inert non-reactive gas or gases.

6. The pharmaceutical preparation of claim 1, wherein the formulation is for human or animal use or for a veterinary use.

7. The pharmaceutical preparation of claim 1, wherein the formulation further comprises a stabilizing agent or a glycerol.

8. The pharmaceutical preparation of claim 1, wherein the pharmaceutical preparation is capable of being re-formulated for final delivery as comprising a liquid, a suspension, a gel, a geltab, a semisolid, a tablet, a sachet, a lozenge or a capsule, or as an enteral formulation.

9. The pharmaceutical preparation of claim 1, wherein the anaerobic microorganism population of (a)(i) or (a)(ii) are free or substantially free of rough fecal particulate matter or non-floral matter.

10. The pharmaceutical preparation of claim 1, wherein the anaerobic microorganism population of (a)(i) or (a)(ii) are initially derived from an individual screened or tested for a disease or infection, or are initially derived from an individual screened to have a normal, healthy or wild type population of fecal flora.

11. The pharmaceutical preparation of claim 1, wherein the anaerobic microorganism population of (a)(i) or (a)(ii) are at least about 90% isolated or pure, or having no more than 1.0% non-fecal floral material.

12. The pharmaceutical preparation of claim 1, wherein the anaerobic microorganism population of (a)(i) or (a)(ii) are formulated for or calibrated for repeat or multiple implantations, administration, delivery or infusions.

13. The pharmaceutical preparation of claim 1, wherein the anaerobic microorganism population of (a)(i) or (a)(ii) are formulated with or mixed with a saline, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent, coloring agent, at least one vitamin, mineral supplement, a dietary supplement, a prebiotic nutrient or any combination thereof.

14. The pharmaceutical preparation of claim 1, wherein the pharmaceutical preparation is made substantially or completely oxygen-free by completely or substantially replacing the air in the pharmaceutical preparation with nitrogen.

15. A product of manufacture, comprising:
(a) a formulation comprising a frozen, freeze-dried, spray-dried, lyophilized or powder-processed entire or at least 90% anaerobic microorganism population of a complete microbiota of a fecal sample,
(b) an oxygen scavenging material, and
(c) an air tight or an anaerobic container,
wherein the product of manufacture provides an at least about 99.5% oxygen-free or oxygen-free containment or storage of the anaerobic microorganism population of (a)(i) or (a)(ii) in the air tight or the anaerobic container.

16. A product of manufacture, comprising:
(a) a formulation comprising entire or at least 90% anaerobic microorganism population of a complete microbiota of a fecal sample in an excipient, a saline, a buffer, a buffering agent or medium, or a fluid-glucose-cellobiose agar (RGCA) medium,
(b) an oxygen scavenging material, and
(c) an air tight or an anaerobic container,
wherein the product of manufacture provides an at least about 99.5% oxygen-free or oxygen-free containment or storage of the anaerobic microorganism population of (a)(i) or (a)(ii) in the air tight or the anaerobic container.

17. The pharmaceutical preparation of claim 1, wherein the formulation is enhanced with one or more additional bacterial species.

18. The pharmaceutical preparation of claim 17, wherein the one or more additional bacterial species are selected from the group consisting of a *Bacteroides* species, a *Firmicutes* species, and *Bacillus thuringiensis*.

* * * * *